US010661039B2

(12) United States Patent
Fuhrman

(10) Patent No.: US 10,661,039 B2
(45) Date of Patent: May 26, 2020

(54) SELF-DEPLOYED CUFF AND SKIRT TRACHEAL TUBE

(71) Applicants: Texas Tech University System, Lubbock, TX (US); Bradley P. Fuhrman, El Paso, TX (US)

(72) Inventor: Bradley P. Fuhrman, El Paso, TX (US)

(73) Assignee: TEXAS TECH UNIVERSITY SYSTEM, Lubbock, TX (US)

(*) Notice: Subject to any disclaimer, the term of this patent is extended or adjusted under 35 U.S.C. 154(b) by 696 days.

(21) Appl. No.: 15/325,795

(22) PCT Filed: Jul. 14, 2015

(86) PCT No.: PCT/US2015/040337
§ 371 (c)(1),
(2) Date: Jan. 12, 2017

(87) PCT Pub. No.: WO2016/010998
PCT Pub. Date: Jan. 21, 2016

(65) Prior Publication Data
US 2017/0203065 A1 Jul. 20, 2017

Related U.S. Application Data

(60) Provisional application No. 62/191,808, filed on Jul. 13, 2015, provisional application No. 62/024,504, filed on Jul. 15, 2014.

(51) Int. Cl.
*A61M 16/04* (2006.01)

(52) U.S. Cl.
CPC .... *A61M 16/0434* (2013.01); *A61M 16/0402* (2014.02); *A61M 16/045* (2014.02);
(Continued)

(58) Field of Classification Search
CPC .............. A61M 16/00; A61M 16/0434; A61M 16/0465; A61M 16/0475;
(Continued)

(56) References Cited

U.S. PATENT DOCUMENTS 3,616,799 A * 11/1971 Sparks ................. A61M 16/04
128/207.15
3,707,151 A 12/1972 Jackson
(Continued)

FOREIGN PATENT DOCUMENTS

WO 2012052908 A1 4/2012

OTHER PUBLICATIONS

IntelliCuff, Product Brochure, Hamilton Medical 2012, retrieved on Dec. 15, 2015, www.hamilton-medical.com/intellicuff, 4 pages.

*Primary Examiner* — Quang D Thanh
*Assistant Examiner* — Jacqueline M Pinderski
(74) *Attorney, Agent, or Firm* — Loza & Loza LLP; Kevin L. Soules

(57) ABSTRACT

A method and system for an endotracheal tube or tracheostomy a tube formed with a hole, a cuff connected to the tube and formed around the hole, and a skirt connected to the tube above the cuff and draped over the cuff. A coating of a hydrophobic, lipophobic, and oleophobic substance can be disposed on the interior and exterior surface of the tube, the cuff, and the skirt. A stylet and siring may be used to secure the skirt during insertion in a detachable fashion. The string is retractable on withdrawal of the stylet.

20 Claims, 10 Drawing Sheets

(52) U.S. Cl.
CPC .... *A61M 16/0447* (2014.02); *A61M 16/0452* (2014.02); *A61M 16/0465* (2013.01); *A61M 16/0484* (2014.02); *A61M 16/0488* (2013.01); *A61M 2205/0238* (2013.01)

(58) Field of Classification Search
CPC .. A61M 16/045–0452; A61M 16/0488; A61M 2205/0238; A61M 16/0484; A61M 16/0447; A61M 16/04–0495; A61B 1/267; A61B 1/2673; A61B 1/2676
USPC ........ 128/207.14, 207.15, 6, 303.1; 138/128, 138/146, 127; 604/282; 250/515.1; 600/120, 183–200
See application file for complete search history.

(56) References Cited

U.S. PATENT DOCUMENTS

| | | | |
|---|---|---|---|
| 3,995,643 A | | 12/1976 | Merav |
| 4,278,081 A | * | 7/1981 | Jones ................ A61M 16/0465 128/207.15 |
| 5,065,757 A | * | 11/1991 | Dragisic ............. A61M 16/04 128/207.14 |
| 2008/0078405 A1 | * | 4/2008 | Crumback ............ A61M 16/04 128/207.15 |
| 2008/0156323 A1 | | 7/2008 | Angel et al. |
| 2011/0048427 A1 | | 3/2011 | Zachar |
| 2011/0073115 A1 | * | 3/2011 | Wood .................... A61M 16/04 128/207.15 |
| 2011/0251509 A1 | * | 10/2011 | Beyhan ............ A61M 16/0463 600/529 |

* cited by examiner

SELF-DEPLOYED CUFF AND SKIRT TRACHEAL TUBE

CROSS REFERENCE TO RELATED APPLICATIONS

This application is the US national phase of International Application No. PCT/US2015/040337, filed on Jul. 14, 2015 under the PCT (Patent Cooperation Treaty), and claims priority to U.S. Provisional Patent Application Nos. 62/191,808, filed Jul. 13, 2015, and 62/024,504, filed on Jul. 15, 2014. The entire contents of these applications are incorporated herein by reference.

FIELD OF THE INVENTION

The embodiments disclosed herein are generally related to methods and systems for endotracheal/tracheostomy tubes.

BACKGROUND

Endotracheal tubes are the principal means by which anesthesia and oxygen are administered to patients requiring secured airways or mechanical ventilation. Traditional endotracheal and tracheostomy tube cuffs are essentially balloons positioned around a tracheal tube. As illustrated in FIG. 1 (labeled "prior art") in previously known endotracheal tubes 100, an inflation conduit is partially embedded in the wall of the tracheal tube, running from the cuff up the side of the endotracheal tube. At the top, the inflation conduit is sealed with a valve or adapter at the inflation port to which a syringe connects for inflation of the cuff. The balloon is inflated after the tube is inserted into the trachea to seal the airway and prevent air leak around the tube and out the mouth or nose.

Traditionally, cuffed tubes often require periodic re-inflation. They suffer from problems with air leaking either out of the cuff or within the airway around the cuff, and risk of over-inflation, which may result in tracheal mucosal ischemia and injury. Vigilant monitoring of conventional endotracheal tubes is required because minimal deflation of the balloon can unseal the airway thereby allowing air to leak. The "air leak" effectively decreases the volume of each breath delivered to the patient and allows backflow of anesthetic gas into the operating suite. Re-inflation of the balloon increases the ever-present risk of over-inflation, which can lead to tracheal injury.

Therefore, a need exists for improved endotracheal tubes that reduce air leak, reduce the chance of over inflation, and reduce the likelihood of injury to the patient being intubated.

SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the disclosed embodiments to provide endotracheal tubes.

It is another aspect of the disclosed embodiments to provide tracheostomy tubes.

It is another aspect of the disclosed embodiments to provide a method and system for ventilation using endotracheal cuffs and endotracheal skirts associated with endotracheal or tracheostomy tubes.

It is another aspect of the disclosed embodiments to provide combined endotracheal cuff and skirt arrangements associated with an endotracheal or tracheostomy tube wherein patient breathing or mechanical ventilation deploys the cuff and skirt arrangement in order to prevent air leak and patient injury.

The aforementioned aspects and other objectives and advantages can now be achieved as described herein. A method and system for an endotracheal tube or tracheostomy tube comprises a tube formed with a hole, a cuff connected to the tube and formed around the hole, and a skirt connected to the tube above the cuff and draped over the cuff. A coating of a hydrophobic, lipophobic, and oleophobic substance can be disposed on the interior and exterior surface of the tube, the cuff, and the skirt.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Endotracheal tubes are a specific variety of tracheal tubes that are inserted into a patient's mouth, or less commonly a patient's nose, in order to create an airway for the patient to inhale oxygen and exhale carbon dioxide, and to provide a path for the administration of drugs and other medical devices. Similarly, tracheostomy tubes are short curved tubes generally inserted in a tracheostomy stoma in order to maintain a patient's airway lumen after a tracheotomy. The embodiments disclosed herein provide tracheal tubes, endotracheal tubes, and tracheostomy tubes with an improved cuff and skirt arrangement to prevent air leak.

Figure 1:
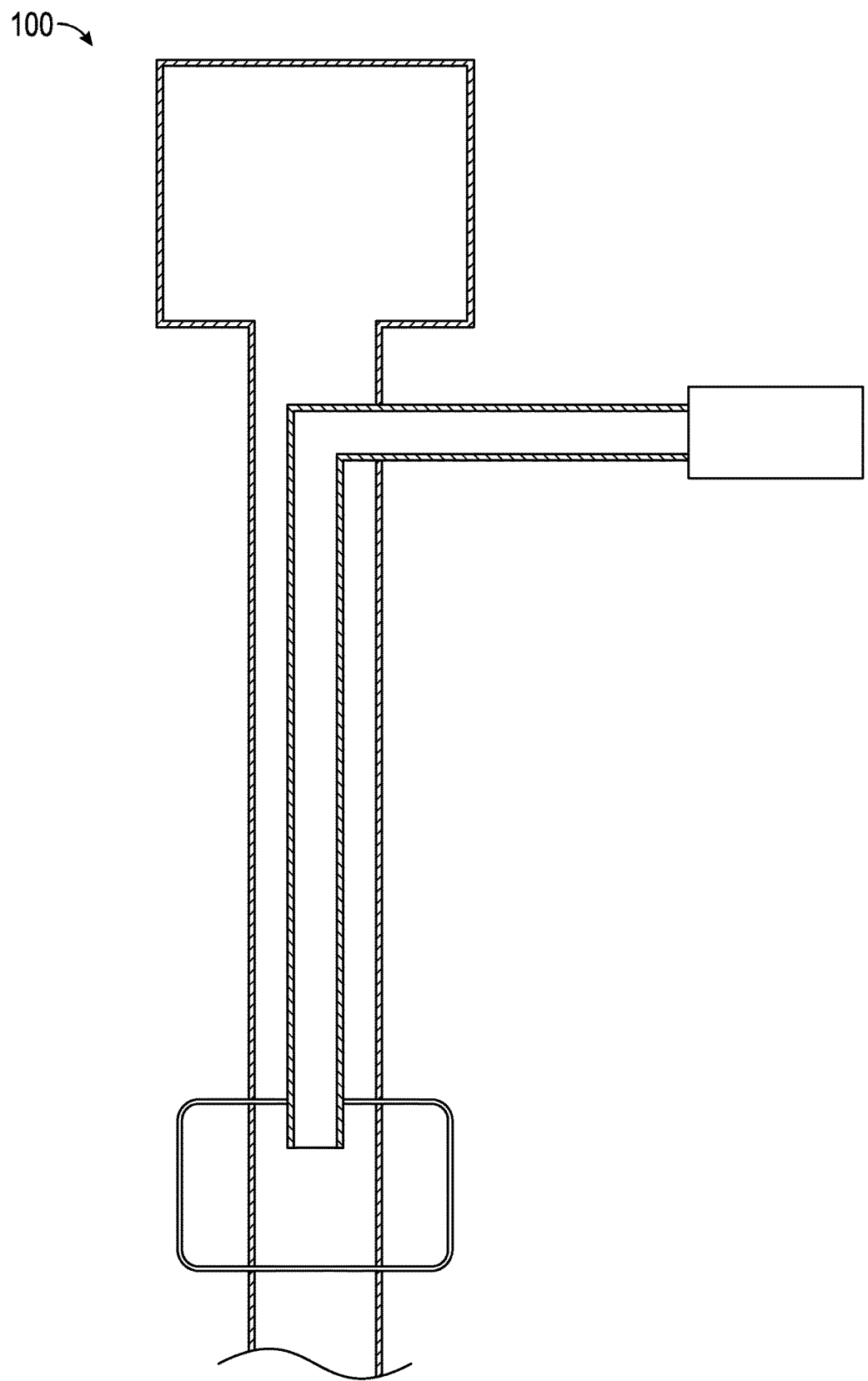
FIG. 1 depicts an endotracheal or tracheostomy tube as understood in prior art embodiments.
Figure 2:
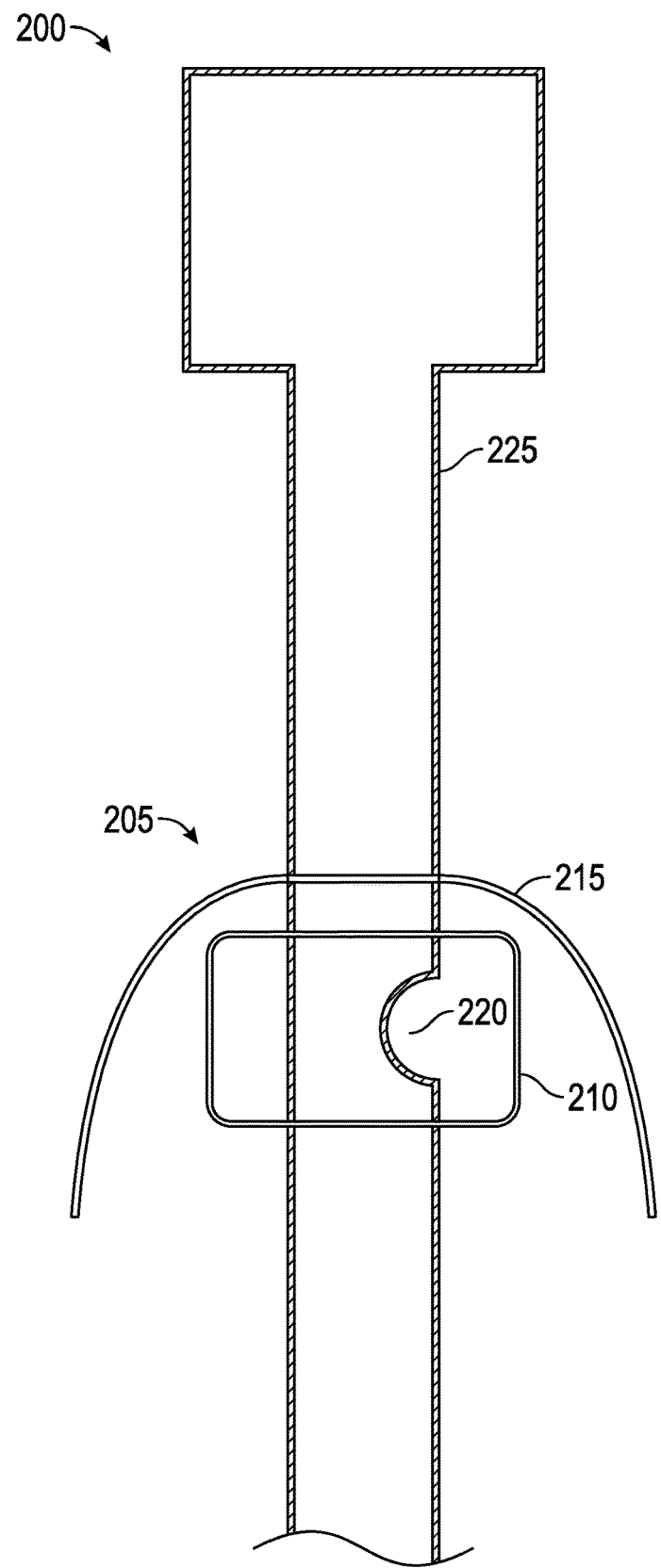
FIG. 2 depicts a block diagram of an endotracheal or tracheostomy tube in accordance with the disclosed embodiments.

FIG. 2 illustrates a self-deploying, self-sealing endotracheal tube 200 in accordance with embodiments disclosed herein. The endotracheal tube 200 includes a combined cuff 210 and skirt 215 to form a cuff and skirt arrangement 205 formed in or on tube 225. The endotracheal tube 200 includes a cuff 210 that can be inflated to create a seal against the patients trachea. However, the cuff 210 is formed with an associated skirt 215 which solves many of the problems associated with traditional endotracheal tubes.

FIG. 2 includes an endotracheal tube 200 with a hole 220 connecting the inside of the tube 225 to the inside of the cuff 210. The cuff 210 is thus sealed to tube 225 around hole 220. The hole 220 allows air to flow through the tube 225 and inflate the cuff 210. In this way, the cuff 210 associated with cuff and skirt arrangement 205 can be inflated solely by patients ventilation. Mechanical means for inflating the cuff are therefore unnecessary (although may be used in certain embodiments). This guarantees that the cuff 210 will not be overinflated.

Endotracheal tube 200 also includes a deployable skirt 215 proximal to and draped over the cuff 210. The skirt 215 is connected to the tube 225 above the cuff 210. When positive pressure is applied to the tracheal tube, for example, during inspiration, it inflates the cuff 210, pressing the cuff 210 against the patient's trachea. The inflated cuff 210 also serves to deploy the skirt 215. The skirt 215 offers a second layer of leak protection further sealing the patients airway. On expiration, positive end expiratory pressure (PEEP) may deflate, or partially deflate, the cuff. However, the positive expiratory pressure holds the skirt 215 in place. Thus, the seal of the skirt 215 to the trachea remains intact.

The combined cuff and skirt arrangement 205 thus provides a trustworthy seal of the patient's airway throughout inspiration and expiration without the risk of over inflation while preventing leak commonly associated with prior art endotracheal tubes such as endotracheal tube 100.

Figure 9:
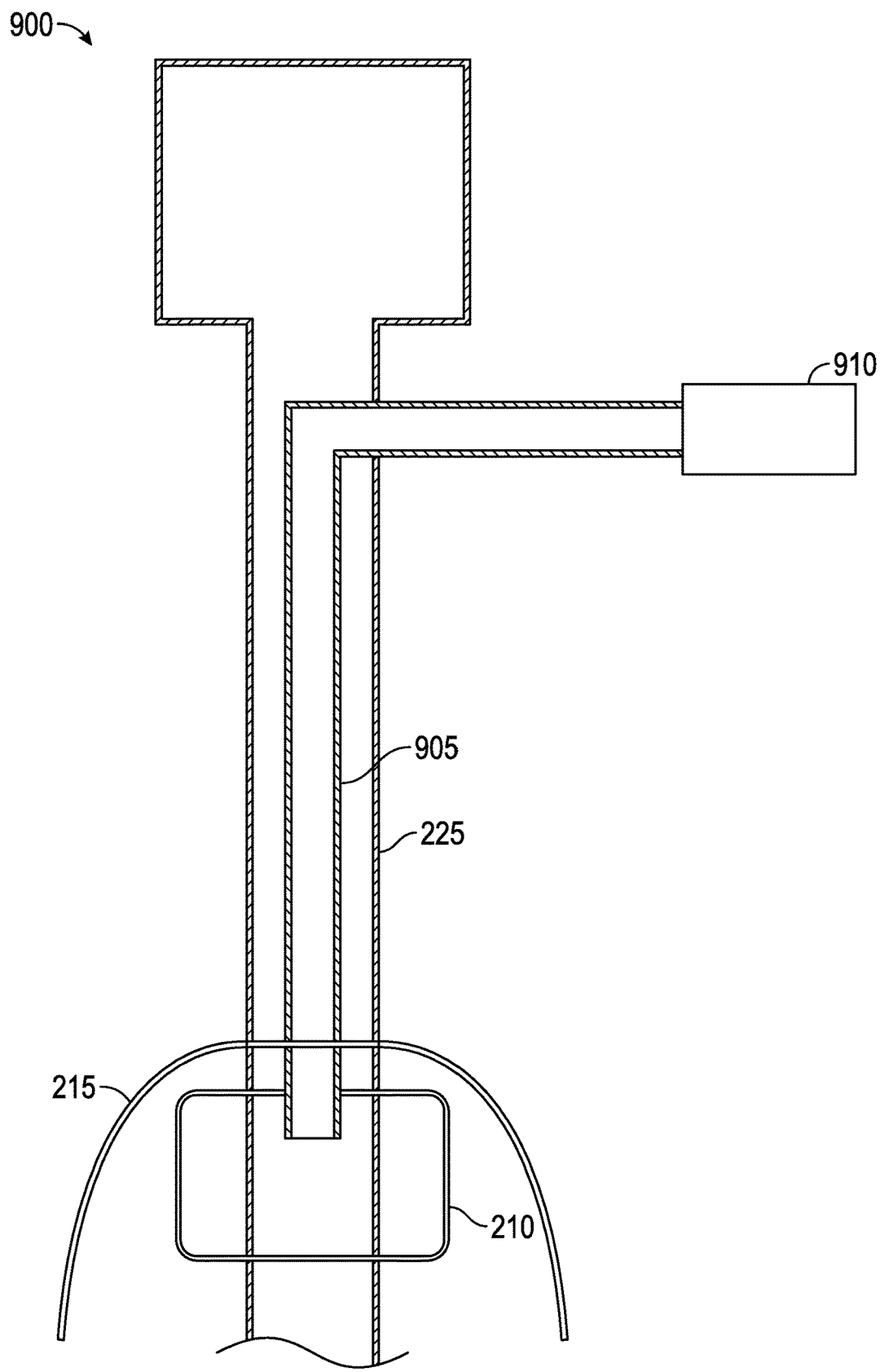
FIG. 9 depicts a block diagram of an alternative embodiment of an endotracheal or tracheostomy tube in accordance with an embodiment of the invention.

FIG. 9 provides an alternative embodiment of a system 900 wherein the cuff and skirt arrangement 205 are deployed using an inflation conduit 905 running along the tube 205. The inflation conduit 905 is operably connected to an inflation port and valve assembly 910. The cuff 210 can be inflated using a syringe or other such apparatus connected to the inflation port 910 and the valve prevents the air from exiting until manually released.

Figure 3:
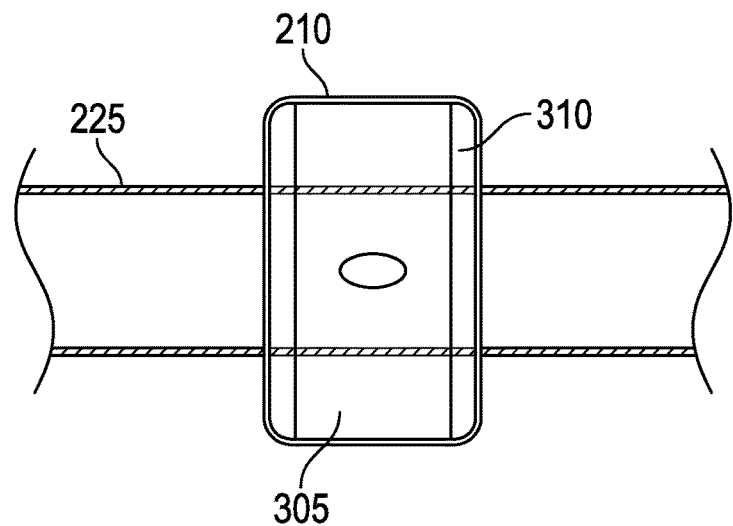
FIG. 3 depicts a view of coated endotracheal cuff in accordance with an embodiment of the invention.
Figure 3:
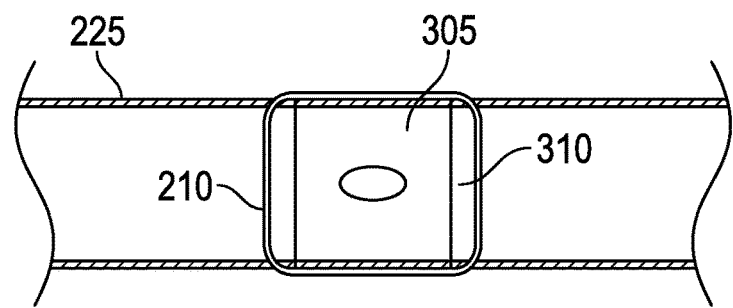

FIG. 3 illustrates specialized coatings 305 that can be applied to the cuff 210, skirt 215, cuff and skirt arrangement 205, and parts of the tube 225 to obviate possible problems with wetting and ensure a proper seal. In particular, wetting can cause fragile parts of endotracheal tubes to stick to one another. This may prevent the necessary positioning and/or deployment of the skirt/cuff combination 205. In FIG. 3, a coating 305 which is formed to be at least one of hydrophobic, lipophobic, and/or oleophobic is applied to the inside and outside of the cuff 210 to prevent sticking. It should be appreciated that the same coating can be applied to surfaces of the skirt 215 and tube 225 as necessary.

Certain surfaces 310, as shown in FIG. 3, may not be coated. These surfaces 310 are excluded because they are the surfaces that are bonded to the endotracheal tube 225 and/or skirt 215. Coatings on these surfaces may prevent proper bonding.

Figure 4:
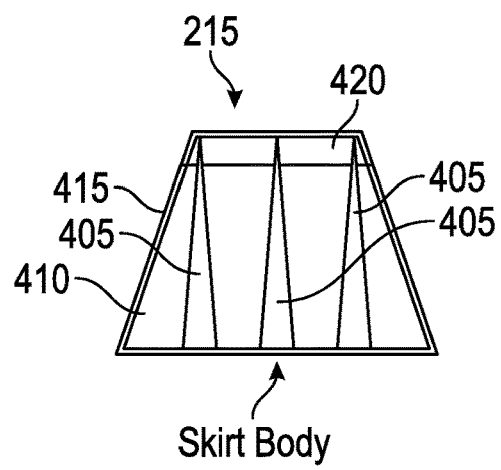
FIG. 4 depicts a view of an endotracheal skirt in accordance with another embodiment of the invention.

The skirt 215 is illustrated in detail in FIG. 4. Skirt 215 can include skirt struts 405 distributed in the skirt body 410. The skirt struts 405 are configured to allow the skirt 215 to fold. The folding facilitates insertion during intubation. Skirt struts 405 are also configured to provide strength and rigidity to skirt 215 in order to prevent inversion.

Skirt inversion may occur when the flimsy skirt material flips up out of position. This may occur for a number of reasons. For example, positive end expiratory pressure may push the skirt 215 beyond its intended position toward the upper end of the trachea. Likewise, during placement or movement of the endotracheal tube, contact with the skirt 215 (particularly as a result of wetting and sticking) may pull the skirt 215 out of position. Skirt inversion disturbs the seal the skirt 215 is intended to create.

Thus, the skirt struts 405 are preferably dispersed into skirt material 415. Skirt struts 405 are preferably wedge-shaped with the wider sections formed at the bottom of the skirt 215. Other skirt strut 405 shapes may also be employed depending on design considerations. The wider sections of skirt struts 405 are formed to decrease the likelihood of inversion by lending strength to skirt material 415. The skirt struts 405 and skirt material 415 can be bonded to the skirt rim 420. The skirt rim 420 is bonded to, or integrated with, the endotracheal tube 225 and serves to hold the skirt 215 in place above the cuff 210 on the tube 225.

Figure 7:
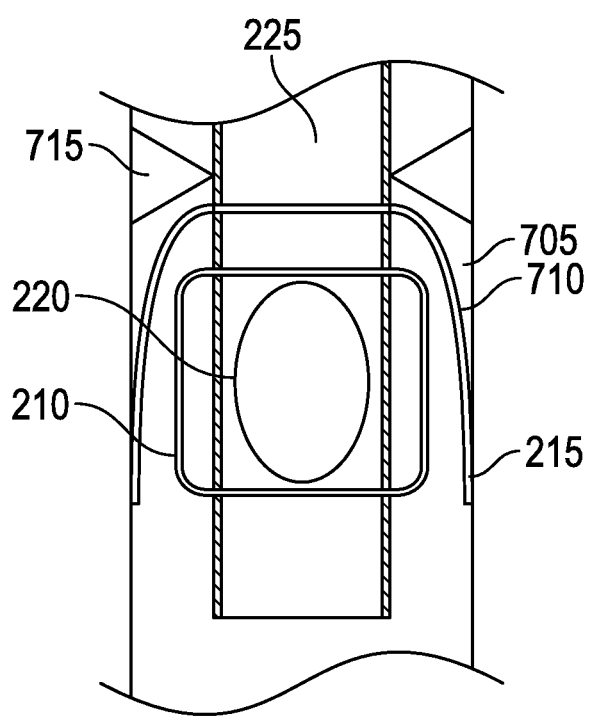
FIG. 7 depicts a diagram of an endotracheal tube positioned in a patient in accordance with another embodiment of the invention.

In one embodiment, the skirt 215 and cuff 210 may be located high on the tube 225. When the endotracheal tube 200 is inserted during intubation, the high placement of the skirt and cuff arrangement 205 allows the skirt 215 and cuff 210 to be positioned just below the subglottic space 705 of the patient's trachea 710 (located below the larynx 715), as shown in FIG. 7. This placement means a longer segment of the tube 225 shaft is left between the cuff 210 and the tracheal opening of the tube 225. The increased distance between the cuff 210 and the tracheal opening also takes advantage of the patient's anatomy to provide a better anatomical location for the skirt 215 in the subglottic region 705.

The increased length between the cuff and tracheal opening serves to increase the pressure drop that develops as gas flows down the longer shaft from the cuff 210 to the tracheal opening. The increased pressure drop ensures more reliable inflation of the cuff 210, skirt 215, and the cuff/skirt arrangement 205. In another embodiment, the tube 225 can be tapered to narrow slightly at its tracheal opening. This also creates a slightly greater pressure difference to more reliably inflate the cuff.

The location of the skirt 215 and cuff 210 below the subglottic space 705 is also intended to take advantage of the natural narrowing of the trachea at the Larynx to provide an additional barrier to prevent inversion of the skirt 215. Specifically, the narrowing at the larynx makes it more difficult for the skirt to invert during PEEP.

Figure 5A:
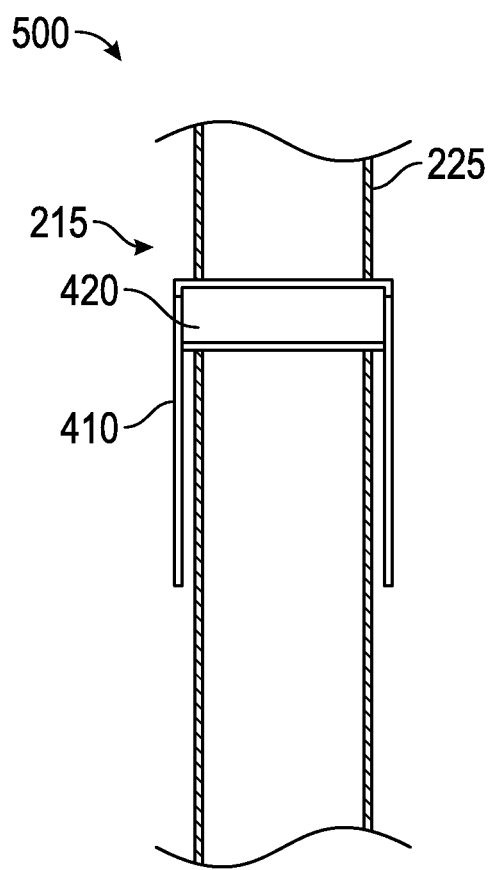
FIG. 5A depicts a diagram of an endotracheal tube during inspiration in accordance with an embodiment of the invention.
Figure 5B:
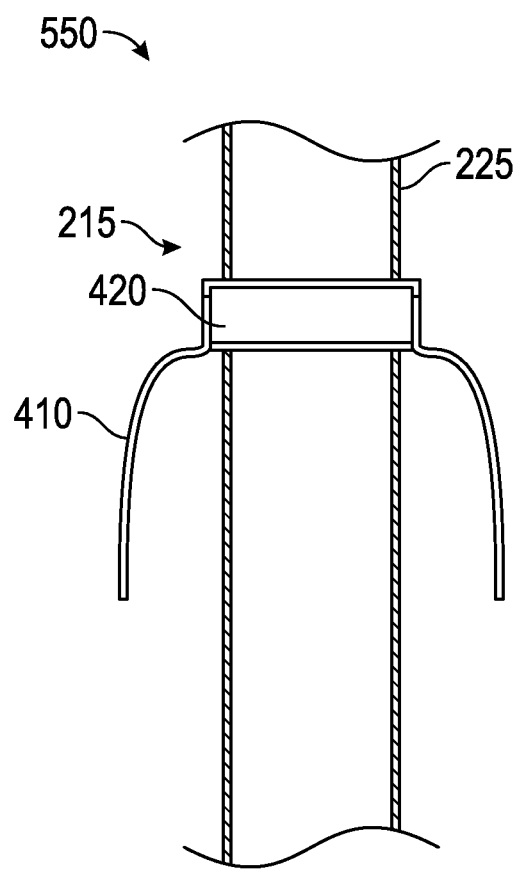
FIG. 5B depicts a diagram of an endotracheal tube during exhalation in accordance with an embodiment of the invention.

FIGS. 5A and 5B illustrate the configuration of the endotracheal tube 200 on insertion 500 (FIG. 5A) and during ventilation 550 (FIG. 5B). Endotracheal tube 200 is inserted before attachment to an inflating apparatus (not shown). During insertion, the combined skirt and cuff arrangement 205 is deflated because the cuff 210 is not being supplied a pressure to inflate the cuff 210. At this stage, the skirt 215 is folded against the cuff 210 and tube 225. Skirt struts 405 facilitate the folded state of skirt 215.

Once ventilation begins, the cuff 210 inflates during inspiration. The inflation of the cuff 210 spreads the skirt 215 creating a seal against the trachea. During expiration positive end expiration pressure is created. The cuff 210 may deflate or partially deflate. However, the positive pressure holds the skirt 215 in place thereby maintaining the seal of the endotracheal tube 200.

Figure 6:
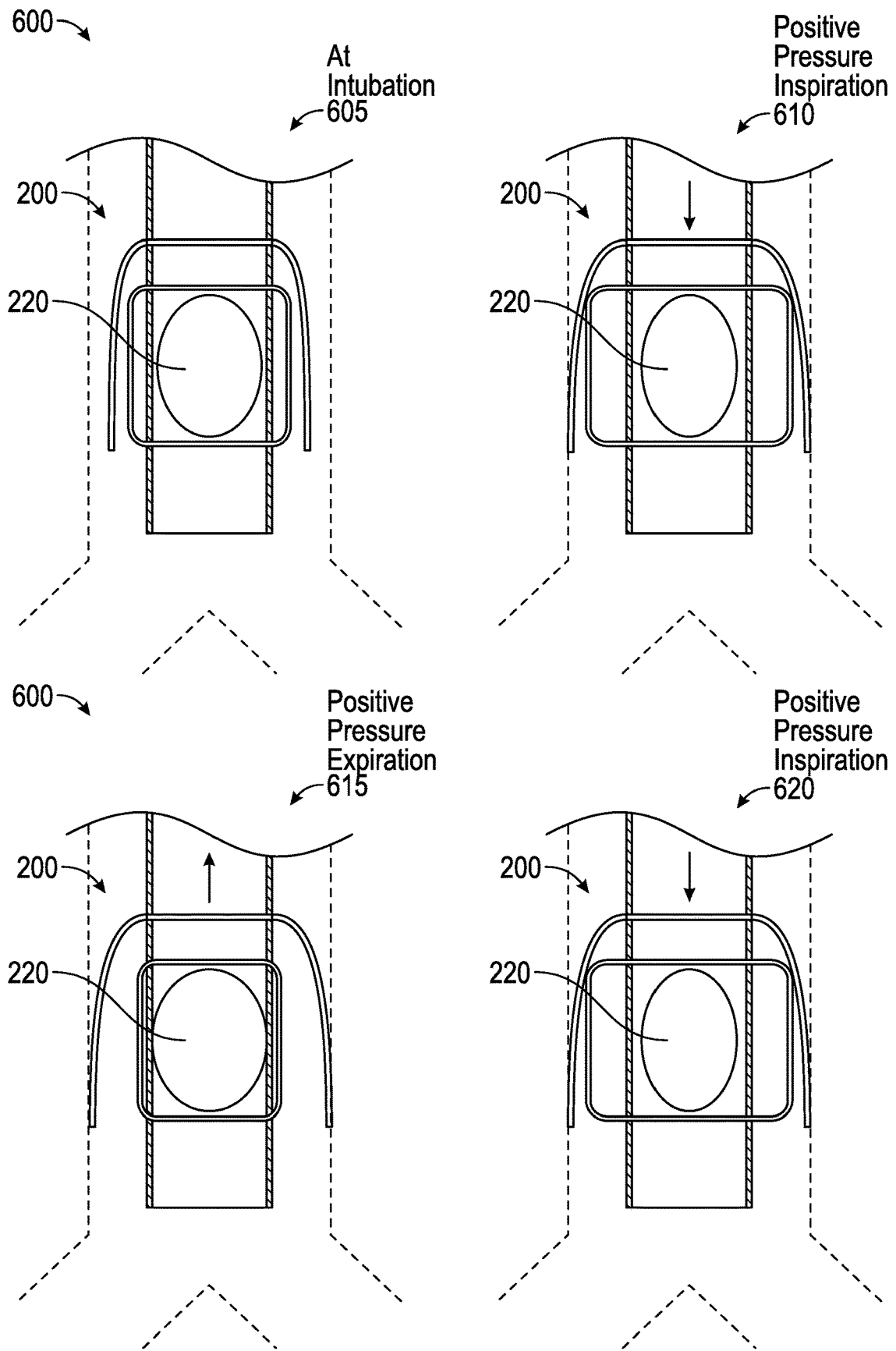
FIG. 6 depicts a diagram of an endotracheal tube during use in accordance with an embodiment of the invention.

FIG. 6 illustrates a view 600 of the combined cuff and skirt arrangement 205 associated with the endotracheal tube 200 at various stages during deployment. At intubation 605, the cuff 210 is deflated and the skirt 215 is not deployed. The skirt 215 is folded down. This allows the apparatus to be easily and properly placed in the patient's trachea, preferably just below the patient's Larynx in the subglottic space.

During inspiration 610, positive pressure in the tube 225 flows into cuff 210 via hole 220 and deploys the cuff 210. The inflation of cuff 210 spreads the skirt 215 creating a tracheal seat From this point, the skirt 215 remains deployed for the duration of ventilation, bypassing any need for inflation, monitoring, or re-inflation.

During expiration 615, some pressure is formed against the bottom side of skirt 215 holding it in place as the patient exhales. Skirt struts 405 prevent inversion of the skirt 215 due to the upward pressure. The process of breathing includes further inspiration as shown by 620. It should be appreciated that additional inspiration and expiration continue, in turn, until the apparatus 200 is removed.

By utilizing normal ventilation pressures during deployment, the device 200 eliminates the risk of tracheal injury from excessive pressure. There is no risk of over-inflation. The cuff and skirt 205 greatly decrease the risk of air leak. Additional benefits include a simplified manufacturing process that does not require embedding an inflation conduit.

Figure 8:
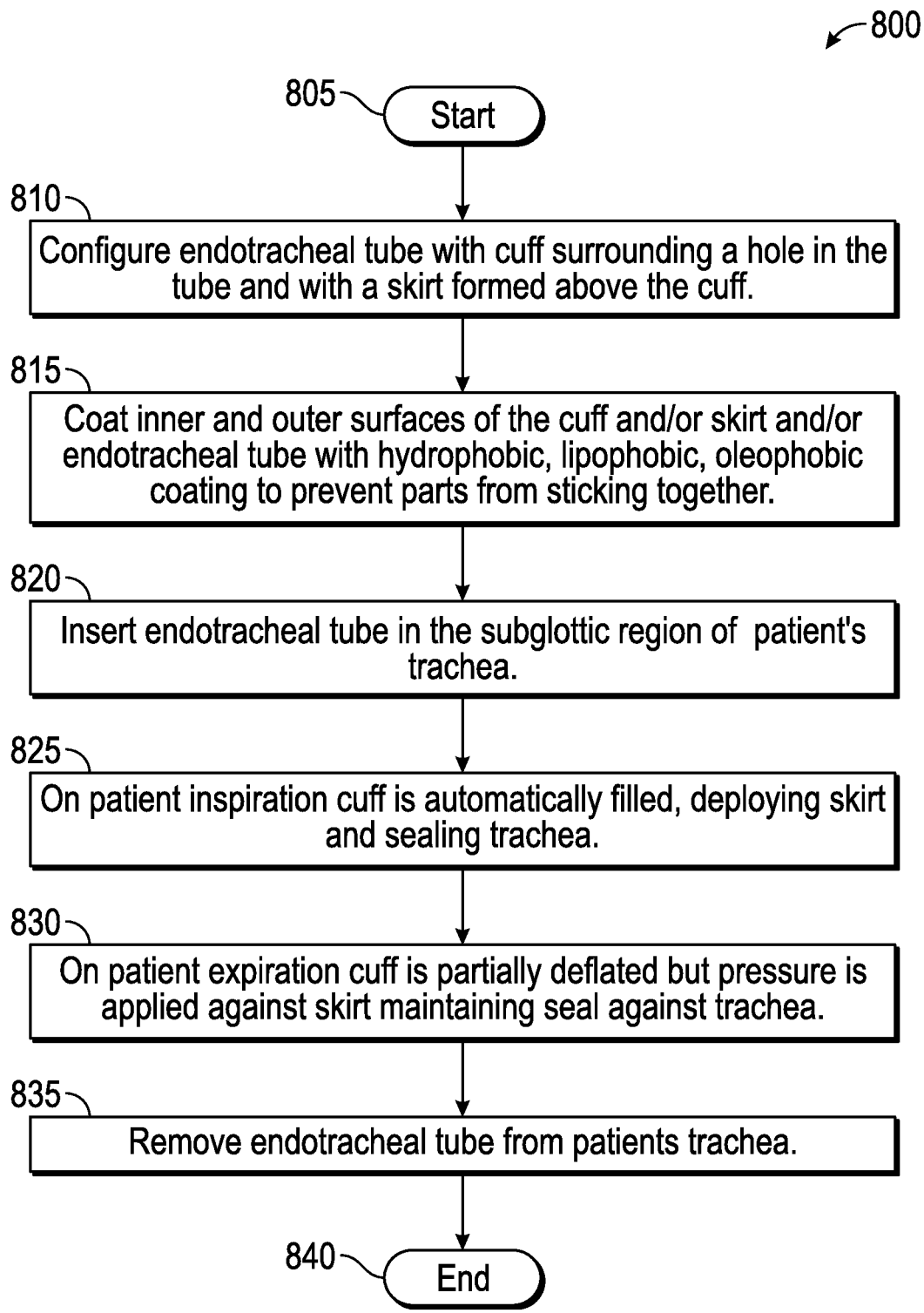
FIG. 8 depicts a flow chart illustrating logical operational steps associated with a method for ventilation associated with an intubated patient in accordance with another embodiment of the invention.

In another embodiment, a method 800 for using the device 200 is shown in FIG. 8. The method starts at step 805.

The self-deployed cuff and skirt tracheal tube is configured to include an endotracheal or tracheostomy tube for use in intubation, as shown at step 810. The endotracheal tube includes a hole surrounded by a cuff and skirt apparatus that is self-deployed at the onset of ventilation. This self-deployment is achieved by the hole, which provides gas to the cuff from airflow through the tube. The inner and outer surfaces of the cuff, skirt, and endotracheal tube can be coated with a hydrophobic, oleophobic, and/or lipophobic coating at step 815. The coating prevents damage to fragile parts that might result from wetting and sticking during deployment.

Next at step 820, the apparatus can be inserted into the subglottic region of the patient's trachea. On inspiration, the cuff is automatically filled as illustrated at step 825. The automatic deployment of the cuff further deploys the skirt forming a safe seal against the patient's trachea. On patient expiration at step 830, the cuff may deflate or partially deflate, but the positive pressure of the expiration holds the skirt in place preventing leaks.

Likewise, at cessation of the procedure (extubation) at step 835, the cuff and skirt apparatus spontaneously retract because only the pressure delivered for ventilation pressurizes the cuff and skirt arrangement. This means of securing and sealing the airway limits mucosal pressure and preserves perfusion of adjacent mucosa by the tracheal capillary bed. The method ends at step 840.

Figure 10A:
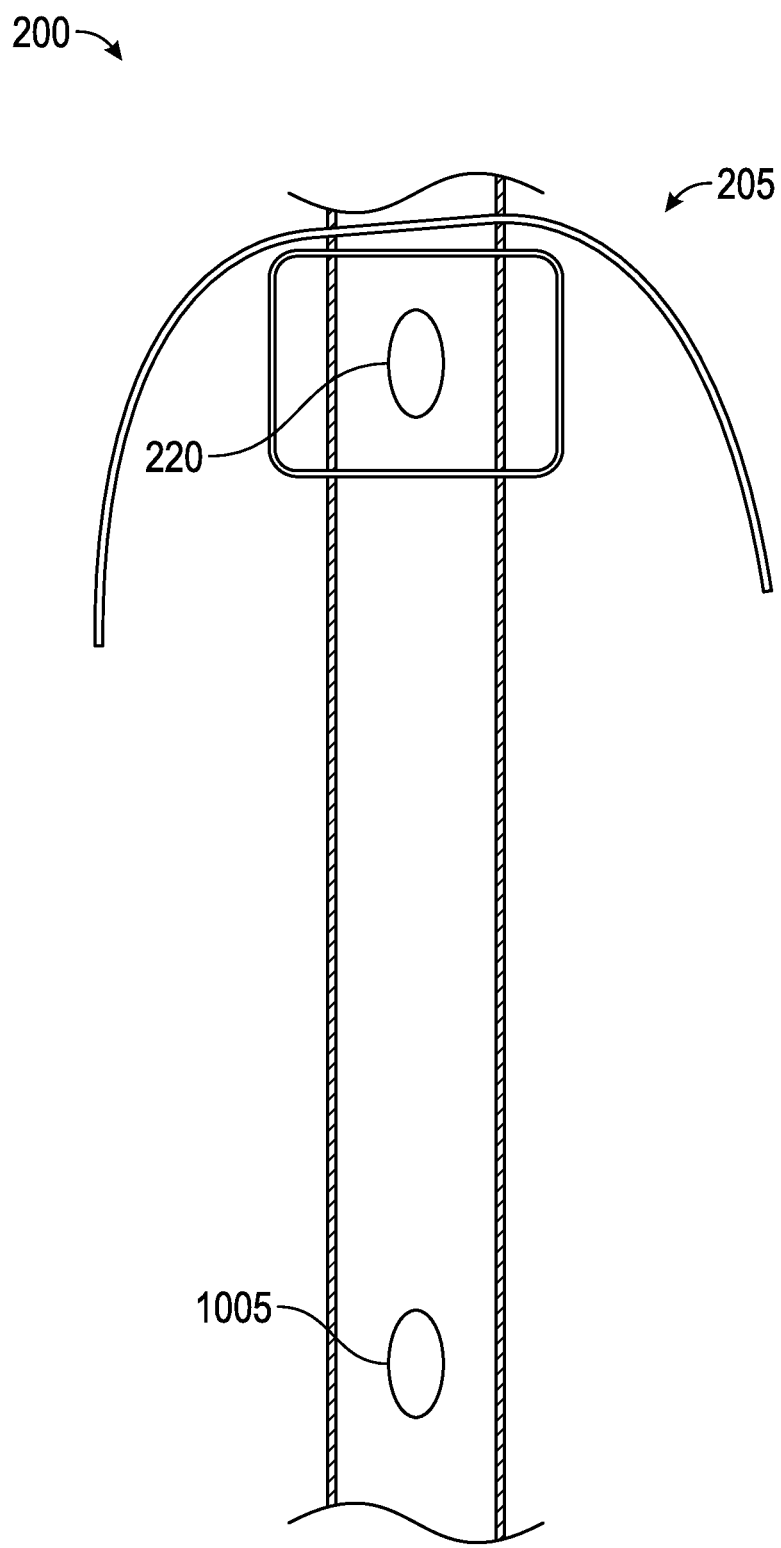
FIG. 10A depicts a block diagram of a endotracheal tube with a Murphy's Eye in accordance with an embodiment of the invention.

FIG. 10A shows an alternative embodiment of the endotracheal tube 200. A Murphy's Eye 1005 may be positioned near the distal end of the endotracheal tube 200 to prevent ventilation of the right lung only, as is commonly the case with endotracheal tubes.

Figure 10B:
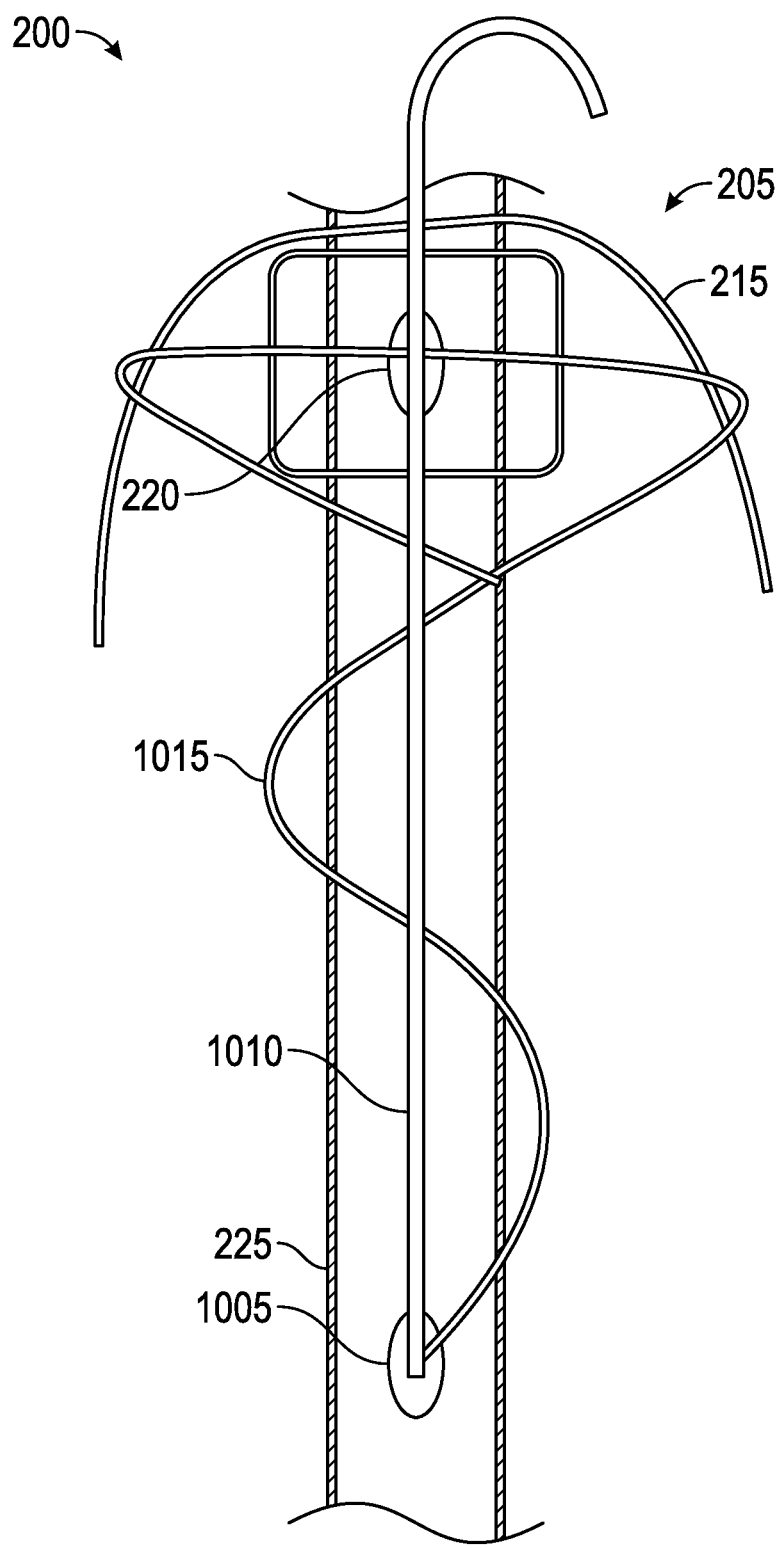
FIG. 10B depicts a block diagram of a stylet assembly associated with an endotracheal tube in accordance with an embodiment of the invention.

FIG. 10B illustrates a stylet 1010 that may be used to insert the endotracheal tube into the airway. The stylet 1010 may be attached to a string 1015. The string 1015 may be embodied as fishing line or other such thin string type material. The string 1015 can detachably anchor the skirt 215 snugly against the tube 225 during insertion. The string 1015 may further traverse the Murphy's Eye 1005 near the tip of the endotracheal tube 200. The string 1015 must be detachable from the skirt 215 and may be retractable. This allows deployment of the skirt 215 when the stylet 1010 is withdrawn to facilitate ventilation of the patient.

Based on the foregoing, it can be appreciated that a number of embodiments, preferred and alternative, are disclosed herein. For example, in one embodiment, a system comprises a tube formed with a hole, a cuff connected to the tube and sealed around the hole, and a skirt connected to the tube above the cuff and draped over the cuff. The tube comprises one of an endotracheal tube and a tracheostomy tube.

In another embodiment, the system further comprises a Murphy's Eye formed at the distal end of said tube. The system further comprises a coating comprising at least one of a hydrophobic, lipophobic, and oleophobic substance formed on at least one of an interior and an exterior surface of at least one of the tube, the cuff, and the skirt. The system also comprises a skirt rim connected to the tube and a plurality of skirt struts formed in the skirt configured to prevent inversion of the skirt.

In an alternative embodiment, the skirt and the cuff are located on the tube for positioning in a subglottic region of a trachea. The tube may include a narrowed distal opening. A stylet and a string may be configured to anchor the skirt, to the tube.

In another embodiment, an airflow can be provided to the cuff via the hole. The airflow results from the inspiration and expiration of a patient.

In another embodiment, a tracheostomy system comprises a cuff connected to an endotracheal tube, an inflation conduit configured to deliver gas to the cuff, and a skirt connected to the endotracheal tube above the cuff and draped over the cuff. The system further comprises a coating comprising at least one of a hydrophobic, lipophobic, and oleophobic substance formed on at least one of an interior and an exterior surface of at least one of the tube, the cuff, and the skirt.

In an alternative embodiment, the tracheostomy system further comprises a skirt rim connected to the tube and a plurality of skirt struts formed in the skirt configured to prevent inversion of the skirt. The system can include a narrowed distal opening of the endotracheal tube.

In yet another embodiment, a ventilation method comprises inserting a device comprising a tube formed with a hole, a cuff connected to the tube and sealed around the hole, and a skirt connected to the tube above the cuff and draped over the cuff into the trachea of a patient; inflating the cuff via the hole during ventilation; deploying the skirt via inflation of the cuff; and sealing the skirt with positive end expiratory pressure. The tube comprises one of an endotracheal tube and a tracheostomy tube.

In another embodiment, the method further comprises coating at least one of an interior and an exterior surface of at least one of the tube, the cuff, and the skirt with a coating comprising at least one of a hydrophobic, lipophobic, and oleophobic substance formed thereon.

The method further comprises connecting a skirt rim to the tube and preventing inversion of the skirt using a plurality of skirt struts formed in the skirt. The method can comprise positioning the skirt and the cuff in a subglottic region of the trachea.

In yet another embodiment, the method comprises increasing a pressure difference by narrowing a distal opening of the tube. The method can further comprise providing the airflow to the cuff via the hole mechanically and deflating the cuff automatically before removal of the cuff.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A system comprising:
    a tube formed with a hole;
    a cuff connected to said tube and sealed around said hole;
    a skirt connected to said tube above said cuff and draped over said cuff; and
    a plurality of skirt struts formed in said skirt, each of said plurality of skirt struts comprising a wedge shape with a wider portion of said wedge shape at a bottom of said skirt;
    wherein airflow is provided through said tube and through said hole to inflate said cuff during patient inhalation.

2. The system of claim 1 wherein said tube comprises one of:
    an endotracheal tube; and
    a tracheostomy tube.

3. The system of claim 2 further comprising a Murphy's Eye formed at a distal end of said tube.

4. The system of claim 3 further comprising:
    a stylet; and
    a string connected to said stylet, said string configured to anchor said skirt to said tube, wherein said string is configured to traverse said Murphy's Eye.

5. The system of claim 2 further comprising: a coating comprising a hydrophobic, lipophobic, and oleophobic substance formed on an interior surface and an exterior surface of said tube, said cuff, and said skirt, respectively.

6. The system of claim 2 further comprising:
    a skirt rim bonded to said tube wherein said plurality of skirt struts are bonded to said skirt rim.

7. The system of claim 2 wherein said skirt and said cuff are located on said tube for positioning in a subglottic region of a trachea.

8. The system of claim 1 wherein inflation of said cuff spreads said skirt and said skirt is configured to be sealed against the patient's trachea by a patient expiration.

9. The system of claim 8 wherein said cuff is configured to deflate upon said patient expiration.

10. The system of claim 1 wherein said skirt is configured to fold against said tube as said tube is inserted into the patient's trachea.

11. A tracheostomy system comprising:
    a cuff connected to an endotracheal tube;
    an inflation conduit configured to deliver gas to said cuff;
    a skirt connected to said endotracheal tube above said cuff and draped over said cuff wherein inflation of said cuff spreads said skirt and said skirt is configured to be sealed against the patient's trachea with a patient expiration, wherein said skirt and said cuff are located on said endotracheal tube for positioning in a subglottic region of said trachea;
    a plurality of skirt struts formed in said skirt, each of said plurality of skirt struts comprising a wedge shape with a wider portion of said wedge shape at a bottom of said skirt;
    a coating comprising a hydrophobic, lipophobic, and oleophobic substance formed on an interior surface and an exterior surface of said endotracheal tube, said cuff, and said skirt, respectively;
    a Murphy's Eye formed at a distal end of said endotracheal tube;
    a stylet; and
    a string connected to said stylet, said string configured to anchor said skirt to said endotracheal tube, wherein said string is configured to traverse said Murphy's Eye.

12. The tracheostomy system of claim 11 wherein said skirt further comprises:
    a skirt rim bonded to said endotracheal tube wherein said plurality of skirt struts are bonded to said skirt rim.

13. A ventilation method comprising:
    inserting a device comprising a tube formed with a hole, a cuff connected to said tube and sealed around said hole, and a skirt connected to said tube above said cuff and draped over said cuff, wherein a plurality of skirt struts are formed in said skirt, each of said plurality of skirt struts comprising a wedge shape with a wider portion of said wedge shape at a bottom of said skirt, into a trachea of a patient;
    inflating said cuff with an airflow through said tube and via said hole during said patient's inhalation;
    deploying said skirt via inflation of said cuff; and
    sealing said skirt with positive end expiratory pressure from said patient's exhalation.

14. The method of claim 13 wherein said tube comprises one of:
    an endotracheal tube; and
    a tracheostomy tube.

15. The method of claim 13 further comprising: respectively coating an interior surface and an exterior surface of said tube, said cuff, and said skirt with a coating comprising a hydrophobic, lipophobic, and oleophobic substance, before inserting said device into said trachea of said patient.

16. The method of claim 13 further comprising:
    preventing inversion of said skirt connected to said tube using said plurality of skirt struts formed in said skirt.

17. The method of claim 13 where inserting said device comprising said tube formed with said hole, said cuff connected to said tube and sealed around said hole, and said skirt connected to said tube above said cuff and draped over said cuff into said trachea of said patient further comprises:
    positioning said skirt and said cuff in a subglottic region of said trachea.

18. The method of claim 13 further comprising:
    increasing a pressure difference between a top opening and a distal opening of said tube.

19. The method of claim 13 further comprising:
    providing the airflow to said cuff via said hole mechanically.

20. The method of claim 13 further comprising:
    deflating said cuff before removal of said tube.

* * * * *